United States Patent [19]

Ingalz

[11] Patent Number: 5,026,388
[45] Date of Patent: Jun. 25, 1991

[54] SINGLE-USE SKIN PUNCTURE DEVICE

[76] Inventor: Thomas J. Ingalz, 1528 Hallcrest Dr., San Jose, Calif. 95118

[21] Appl. No.: 412,511

[22] Filed: Sep. 26, 1989

[51] Int. Cl.$^5$ .......................................... A61B 17/32
[52] U.S. Cl. ................................................ 606/182
[58] Field of Search ............... 606/181, 182; 128/637, 128/638; 604/46, 136, 137, 156, 157

[56] References Cited

U.S. PATENT DOCUMENTS

| | | | |
|---|---|---|---|
| 3,623,475 | 11/1971 | Sanz et al. | 604/46 |
| 4,375,815 | 3/1983 | Burns | 606/182 |
| 4,416,279 | 11/1983 | Lindner et al. | 128/314 |
| 4,527,561 | 7/1985 | Burns | 606/182 |
| 4,580,564 | 4/1986 | Andersen | 128/314 |
| 4,637,403 | 1/1987 | Garcia et al. | 128/770 |
| 4,653,513 | 3/1987 | Dombrowski | 606/182 |
| 4,715,374 | 12/1987 | Maggio | 128/314 |
| 4,787,398 | 11/1988 | Garcia et al. | 128/770 |
| 4,794,926 | 1/1989 | Munsch et al. | 128/314 |
| 4,817,603 | 4/1989 | Turner et al. | 606/182 |

*Primary Examiner*—C. Fred Rosenbaum
*Assistant Examiner*—William Lewis
*Attorney, Agent, or Firm*—Schneck & McHugh

[57] ABSTRACT

A single-use puncture device having an escapement assembly, a cylindrical sidewall and a helical spring encircling a lance. The escapement assembly includes cantilevered catch members which abut a stop turn of the helical spring to hold the helical spring in a stressed condition. Pressure at the front end of the puncture device causes a deformation of a thin diaphragm which supports the cantilevered catch members at ends opposite the abutment to the stop turn. The deformation is a flexing which moves the catch members radially outwardly to release the stop turn. The spring thrusts the lance forwardly from an armed position to a propelled position in which the puncture point of the lance extends from the front end of the device. The helical spring thereafter recoils to locate the lance in a neutral position encased within a housing. Rearmament of the device is thereby prevented. The front end of the puncture device includes the central access aperture, a skin-engagement region outward of the access aperture, a raised annulus which defines the skin-engagement region, and the thin flexible diaphragm.

18 Claims, 2 Drawing Sheets

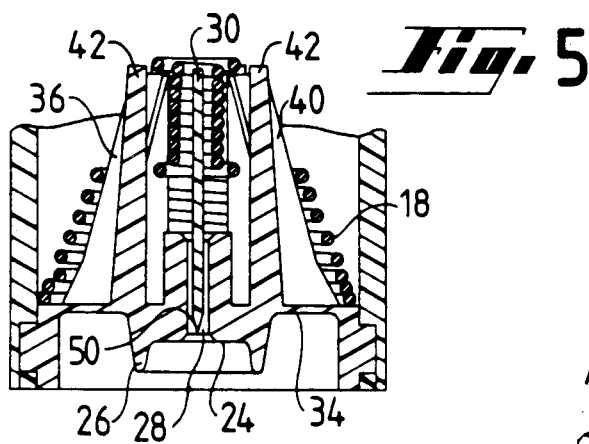
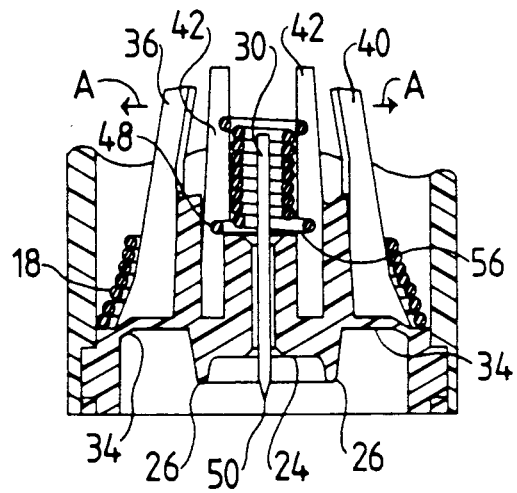
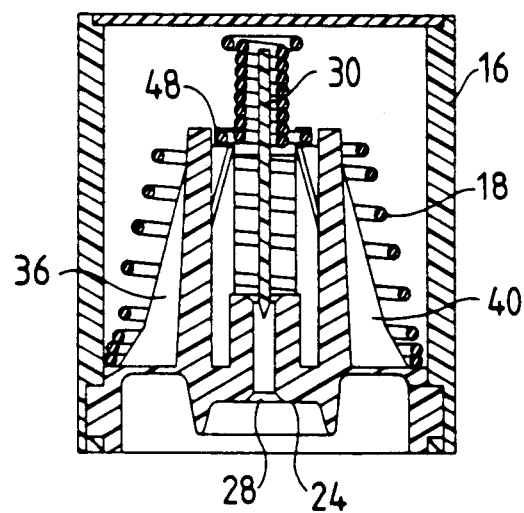
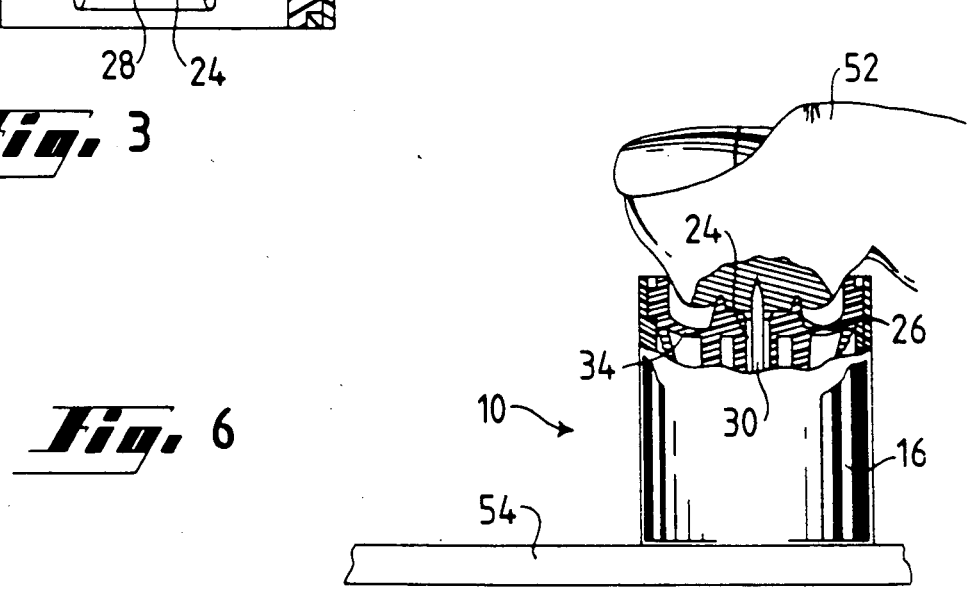

SINGLE-USE SKIN PUNCTURE DEVICE

1. Technical Field

The present invention relates generally to devices for obtaining a blood sample and more particularly to devices for puncturing an individual's finger, ear lobe or heel for diagnostic purposes.

2. Background Art

The processing of blood assays for diagnostic purposes has largely been carried out within centralized diagnostic clinical laboratories. Blood tests typically require samples taken from a vein draw of whole blood. In recent years, new systems have emerged for alternate site markets. Increasingly, testing is performed within a doctor's office, mobile units, geriatric care homes, drug stores, and even the patient's home. Home monitoring of blood glucose levels for diabetics is one example of self-testing. Each such self test requires a droplet or two of fresh finger-puncture whole blood.

Consumable finger lance devices for puncturing the skin of a patient are known. Lance needles are typically installed into pen-like devices which are spring loaded and push-button actuated. Such devices can be easily reused despite warnings against reuse. A first use may contaminate the lance of the device, whereafter the second use may cause the contamination to enter the system of the patient. Within mobile units for testing of such things as cholesterol, an accidental or purposeful reuse can result in cross-contamination of patients.

Another risk involved in drawing blood from a patient is accidental puncturing of hospital personnel in the removal or disposal of lance needles from puncturing devices. Serious health hazards result from such accidental post-use puncturing.

A less dangerous concern involves apprehension of the user who anticipates that pain will occur upon actuation of a release button. U.S. Pat. Nos. 4,416,279 to Lindner et al. and 4,580,564 to Andersen teach devices to lessen the apprehension of the user. The Lindner et al. patent uses an actuating method in which there is no clear indication when a plunger will be triggered so that apprehension is reduced. Anderson uses a weight to force the lance into a user, teaching that elimination of a trigger reduces trauma.

An object of the present invention is to provide a puncture device which is restricted to a single use and which completely encloses a lance to prevent accidental secondary puncturing. Another object is to provide such a device which is inexpensively manufactured and which reduces patient trauma and discomfort.

SUMMARY OF THE OBJECT

The above objects have been met by a puncture device which has a spring that is armed during manufacture of the device and which cannot be rearmed. The puncture device is actuated by a user compressing that area of the device through which the lance extends for piercing the skin of the user. The spring propels the lance temporarily from the housing of the device, afterwhich the spring again draws the lance within the housing. The spring is initially triggered as a result of deformation, but relaxation of the spring disposes the lance such that the deformation does not permit post-use contact between a user and the lance.

The single-use puncture device includes a housing having a cylindrical rigid sidewall. At the front end of the housing, is a skin-engagement region which is attached to the sidewall by a thin diaphragm. The diaphragm permits flexing, so that pressure on the skin-engagement region causes axial movement of that region into the cylindrical sidewall. A plurality of catch members are cantilevered from the diaphragm so that flexing of the diaphragm causes spreading of the cantilevered ends of the catch members.

The spring has a first end which is in fixed relation to the housing and has a free end which secures the lance. The spring is a helical spring which encircles the lance. In the quiescent state, the cantilevered ends of the catch members contact a turn of the spring to hold the spring in a stressed condition for storage of potential energy. In the stressed condition the spring holds the lance in an armed position within the housing and in alignment with the access aperture. As noted above, pressure at the skin-engagement region causes spreading of the cantilevered ends of the catch members to release the spring. The spring displaces the lance from the armed position to a propelled position in which at least a portion of the lance extends through the access aperture to pierce the skin of the user. The spring then recoils to draw the lance back into the housing and into a neutral position.

An advantage of the present invention is that the skin-engagement region prepares the skin for lancing. A force is required to initiate actuation and that force is such that a raised perimeter about the region produces an on-target skin bulge toward the access aperture. The bulge increases the susceptibility of the target area to skin lancing. A relatively high-quality wound is therefore assured. Moreover, the perimeter pressure into the tissue of the user limits sensitivity so that discomfort during lancing of the skin is reduced.

Another advantage is that a lance and the spring are completely enclosed within the housing, preventing a user from arming the puncture device for a second use. The lance is removed from the skin-engagement region by a distance exceeding possible deformation at the thin diaphragm. The device cannot be rearmed and post-use punctures are not possible. Yet another advantage of the present invention is that user apprehension is lessened since, unlike puncture devices having a trigger apparatus, a user is unable to precisely predict when the present invention will trigger. Another advantage is that the device includes a tamper-resistant cover which is fixed to the housing in a manner which requires a user to damage the cover during removal. Thus, after the cover has been removed, the fact that removal has taken place is evident. Moreover, the cover can be used as an analgesic or astringent-treated bandage.

BRIEF DESCRIPTION OF THE DRAWINGS

FIG. 3 is a side sectional view of the puncture device of FIG. 2 shown in an armed condition.

FIG. 4 is a side sectional view of the puncture device of FIG. 2 shown in a propelled condition.

FIG. 5 is a side sectional view of the puncture device of FIG. 2 shown in a normal position.

FIG. 6 is an operational view of the puncture device of FIG. 4.

BEST MODE FOR CARRYING OUT THE INVENTION

Figure 1:
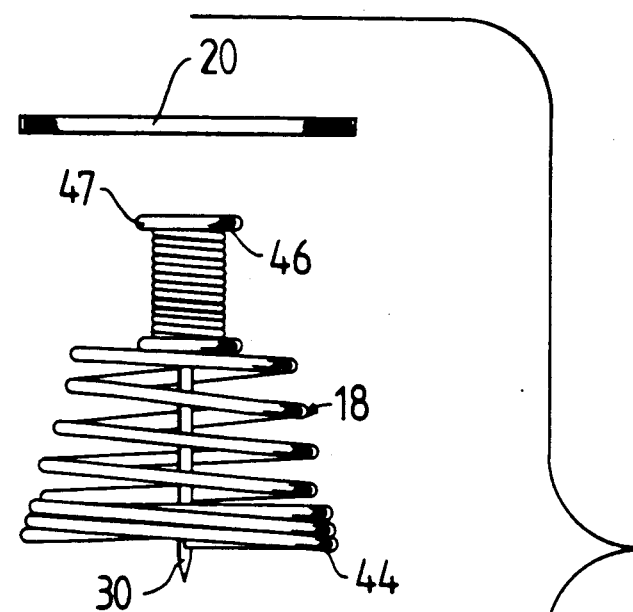
FIG. 1 is a side exploded view of a single-use puncture device in accord with the present invention.
Figure 2:
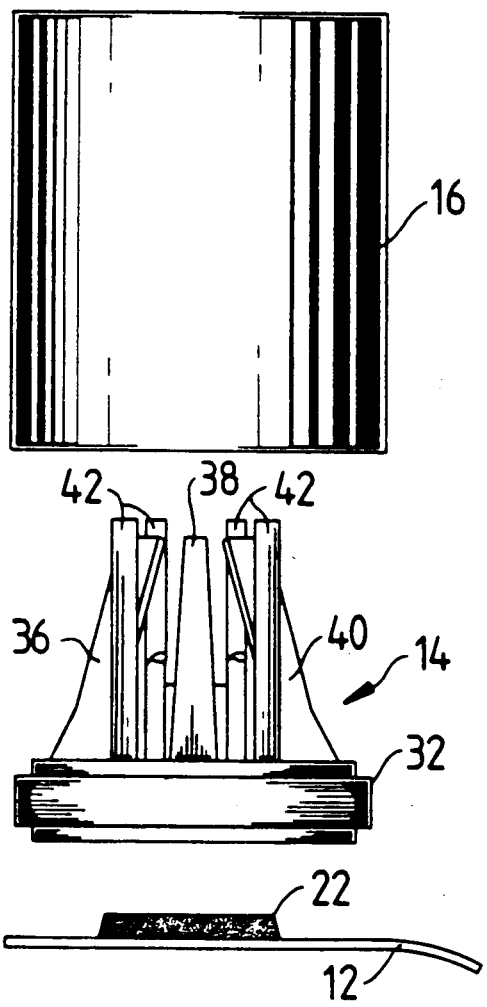
FIG. 2 is a side, partially sectional view of the puncture device of FIG. 1.
Figure 2:
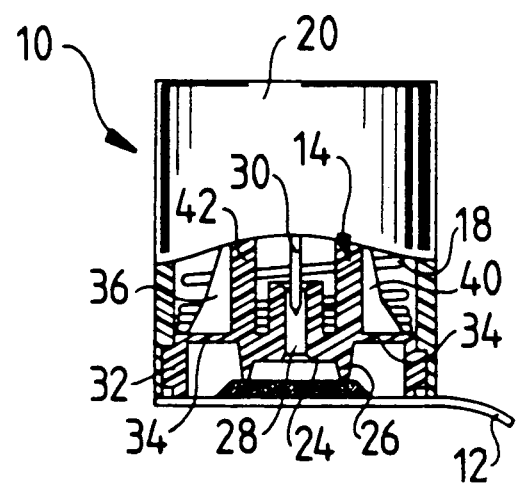

With reference to FIGS. 1 and 2, a single-use puncture device 10 is shown as including a front cover 12, an escapement assembly 14, a cylindrical housing 16, a helical spring 18 and a rear cover 20. Both the front and the rear cover 12 and 20 are affixed to the cylindrical side housing 16 in a manner to prevent undetected removal. The rear cover is permanently attached or is an integral part of the side housing 16, while the front cover 12 may be removed with a detectable amount of damage to the front cover. In this manner, the puncture device is tamper-resistant. The front cover includes an analgesic or astringent pad 22.

The escapement assembly 14 has a skin-engagement region 24, as best seen in FIG. 2. At the perimeter of the skin-engagement region is a raised annulus 26. At the center of the skin-engagement region 24 is an access aperture 28 which permits reciprocal movement of a lance 30. A radially expanded rim 32 snugly fits the escapement assembly 14 within the cylindrical side housing 16. A thin diaphragm 34 links the skin-engagement region 24 to the cylindrical side housing 16 by means of the radially expanded rim 32.

Returning to FIG. 1, three catch members 36, 38 and 40 are cantilevered on the escapement assembly 14. Between the cantilevered catch members 36-40, are six parallel poles 42 which, as will be explained more fully below, function to ensure that the lance 30 moves colinearly when the helical spring 18 is triggered.

The cylindrical side housing 16 is a tubular member made of a polypropylene. While the cylindrical shape is preferred, such a shape is not critical. Alternatively, the side housing may be rectangular. The cylindrical is preferred since that shape is less likely to affect operation of the puncture device and since the cylindrical shape facilitates packaging of a number of puncture devices within a single closure.

The helical spring 18 is fixed at one end 44 to the cylindrical side housing 16. The lance 30 is welded to the close wound segment 46 of the helical spring. Thus, motion of the free segment 46 of the helical spring is translated to the lance. The spring preferably includes a series of additional turns, not shown, about an upper-most turn 47. The additional turns contribute to the mass of the spring, thereby providing a greater delivery force. Typically, the spring 18 is made of tempered stainless steel, but this is not critical. The lance 30 may be of any of the types commonly used in the art. The choice of using a lance needle or a lance blade depends upon such factors as the quantity of blood needed for a sample and the callus of a user's finger.

In FIG. 3, the helical spring 18 is shown in a stressed condition to hold the lance 30 in an armed position. The helical spring has a stop turn 48 which rests against the cantilevered catch members 36, 38 and 40. In the stressed condition of FIG. 3, potential energy is stored for propelling the lance forwardly. The puncture point of the lance remains within the access aperture, but at an end opposite the skin-engagement region 24.

In FIG. 4, pressure has been exerted on the raised annulus 26 to cause deformation at the thin diaphragm 34 of the escapement assembly. The deformation is shown as a flexing of the thin diaphragm. The cylindrical shape of the assembly promotes axial movement of the assembly as the diaphragm 34 is stressed by the user. The flexing causes the ends of the cantilevered catch members 36-40 that are opposite the thin diaphragm 34 to move radially outwardly as shown by arrows A. The radially outward displacement releases the stop turn 48 of the helical spring 18 from the catch members. The release of potential energy thrusts the lance 30 forwardly past the neutral position of the spring. The puncture point 50 of the lance thereby ejects beyond the skin-engagement region 24 for the lancing of a user's finger.

The six parallel posts 42 promote linear movement of the lance 30. The parallel posts define a cylindrical volume having a diameter slightly greater than the diameter of the stop turn 48. Thus, the parallel posts 42 act as guides for the stop turn. Preferably, the pair of parallel posts between a pair of cantilevered catch members 36-40 is on pedestals, not shown, which space the base of the poles away from the thin diaphragm 34. The three pedestals are added to assure colinear motion of the posts when the diaphragm is stressed by the user.

After the lance 30 has pierced the skin of the user, the spring 18 recoils to extract the puncture point 50 from the user. The device does not return to the armed position of FIG. 3, but rather stops in the neutral position shown in FIG. 5. The potential energy at initiation of the relaxing of the spring 18 is less than the potential energy stored in the spring when in the armed position. Therefore, the stop turn 48 does not rise to the level of the cantilevered ends of the catch members 36-40. In the neutral position of FIG. 5, the puncture point 50 of the lance 30 is spaced apart from the mouth of the access aperture 28 by a distance greater than the flexure permitted by the thin diaphragm 34. In this manner, post-use compression at the raised annulus 26 does not result in secondary punctures and cannot rearm the puncture device.

In operation, as best seen in FIG. 6 there is a degree of skin preparation prior to puncturing of a user's skin. The puncture device may be pressed against a surface 54 or may be pinched between a finger 52 and thumb of a user. The force required to initiate actuation is such that the contact pressure of the raised annulus 26 against the finger 52 limits sensitivity in the region of the finger to be lanced. The force is typically between 0.5 pound and 1 pound, but cannot be predicted with any certainty. This uncertainty lessens the apprehension of the user since the user is unable to predict with any exactness when the device will trigger. The perimeter pressure also produces an on-target finger bulge toward the skin-engagement region 24 to ensure a quality wound yielding the needed droplets of blood without a need for milking the finger.

Moreover, the recessed nature of the skin-engagement region 24 acts to prevent unintended triggering of the puncture device 10. Only a ridged appendage will trigger the device and the compression must be primarily along the axis of the puncture device. Casual handling of the device is unlikely to cause triggering.

While the present invention has been described as puncturing a fingertip, often it is the side of the finger or even an ear lobe which is punctured. The configuration in operation of the single-use puncture device 10 permits such use. Moreover, the puncture device may be used for infant heel-puncture bleeding. Typically, limiting lance penetration to a depth of 2.4 mm is suitable, but this is not critical since optimal depth may vary with intended use. Because the skin-engagement region 24 preferably has a contour which is adapted to that portion of individual's anatomy which is to be punctured, different puncture devices are needed for puncturing a heel, a finger and an ear lobe. Alternatively, the escapement assembly of the puncture device may be rotatably coupled to the cylindrical side wall 16, and as a rotation is initiated a cam-stop may be used to change the contour of the skin-engagement region or to change the maximum displacement of the lance 30 from the puncture device. For example, referring to FIG. 4, in order to vary the maximum displacement of the lance 30, the stop turn 48 could be less than a 360° turn and the stop turn limit surface 56 could have two or more elevation steps. Rotation of the escapement assembly would then permit selection of alignment of the reduced stop turn with the different elevation steps of the stop turn limit surface.

Returning to FIG. 1, the analgesic or astringent pad 22 of the front cover 12 may be used to clean, desensitize or constrict the target area of a finger prior to actuation and may be used to cover the lanced skin after the blood sample has been obtained. An astringent pad reduces post-puncture bleeding. This advantage is particularly important to those persons who might otherwise experience prolonged bleeding because of an abnormality in blood-clotting factors.

I claim:

1. A single-use skin puncture device comprising,
   a housing having a skin-engagement region and an access aperture through said skin-engagement region, said housing further having a sidewall and a flexible diaphragm connecting said skin engagement region to said sidewall at a front end of said housing, the application of force at said skin-engagement region causing deformation of said diaphragm about said skin-engagement region, said deformation defining a limited range of motion of said skin-engagement region relative to said sidewall,
   movable lance means aligned with said access aperture for piercing skin, said lance means having a puncture point having an armed position within said housing, a neutral position within said housing and a propelled position wherein said puncture point is at the exterior of said housing,
   spring means coupled to said lance means for displacing said puncture point in and out of said housing, from said armed position to said propelled position, and
   catch means for releasably holding said spring means in a condition in which potential energy is stored for said displacing of said puncture point, said spring means coupled to said housing in a manner to release said spring means in response to said deformation, said spring means moving toward a relaxed condition after said displacing to locate said puncture point in said neutral position spaced apart from said skin-engagement region by a distance exceeding said limited range of motion of the skin-engagement region.

2. The single-use puncture device of claim 1 wherein said spring means is a helical spring encircling a portion of said lance means.

3. The single-use puncture device of claim 1 wherein said sidewall is generally cylindrical.

4. The single-use puncture device of claim 3 wherein said catch means is a plurality of catch members contacting said spring means to hold said spring means in said position to store potential energy, said catch members being displaced from said spring means by said deformation of said diaphragm.

5. The single-use puncture device of claim 4 wherein said spring means is a helical spring having a stop turn, said stop turn being in contact with said catch members prior to said deformation.

6. The single-use puncture device of claim 1 wherein said lance means is one of a lance needle and a lance blade.

7. A puncture device comprising,
   an elongated housing having a generally cylindrical rigid sidewall and a skin-engagement region at the front end,
   movable lance means disposed within said housing,
   a spring connected to said housing for propelling said lance means to extend a portion of said puncture means through said skin-engagement region,
   catch means for releasably holding said spring in a stressed position for said propelling of said lance means, and
   trigger means, fixed at opposed ends to said rigid sidewall and said skin-engagement region, for releasing said spring from said catch means, said trigger means being a deformable member diagonal to allow flexure of said front end into a concave position relative to said rigid sidewall, said flexure defining a range of relative motion between said skin-engagement region and said rigid sidewall, said spring being disposed such that relaxation of said spring following said release spaces apart said lance means from said skin-engagement region by a distance greater than said range of relative motion.

8. The puncture device of claim 7 wherein said trigger means is a flexible diaphragm.

9. The puncture device of claim 8 wherein said diaphragm is an annular member.

10. The puncture device of claim 8 wherein said catch means is a plurality of catch members connected to said diaphragm at a first end and to said spring at a second end, flexing of said diaphragm causing lateral movement of said catch members to release said spring.

11. The puncture device of claim 7 wherein said spring is a helical spring encircling said lance means.

12. A single-use puncture device comprising,
   a housing having a rigid sidewall and a front end, said front end having a deformable region made of a flexible material and having a skin-engagement region, said skin-engagement region being displaced axially upon application of axial force at said front end, said front end having an access aperture therethrough,
   lance means disposed within said housing in alignment with said access aperture,
   a spring having a first end attached to said housing and having a free end, said free end coupled to said lance means, and
   a plurality of catch members connected to said front end of said housing and disposed to hold said spring in a stressed condition for storage of potential energy, said catch members being displaced by axial deformation of said front end to release said spring, thereby causing said spring to propel a portion of said lance means through said access aperture, said spring having a relaxed condition in which said lance means is encased within said housing and is spaced apart from said skin-engagement region by a distance exceeding said axial displacement of said skin-engagement region.

13. The puncture device of claim 12 wherein said lance means is a lance needle.

14. The puncture device of claim 12 wherein said sidewall has a cylindrical shape and wherein said front end has a central skin-engagement region connected to said sidewall by a flexible diaphragm.

15. The puncture device of claim 14 wherein said skin-engagement region includes a raised annulus and a depressed area within said raised annulus.

16. The puncture device of claim 14 wherein said flexible diaphragm has an annular configuration.

17. The puncture device of claim 12 wherein said spring is a helical spring encircling said lance means.

18. A single-use skin puncture device comprising,
- a housing having a skin-engagement region and an access aperture through said skin-engagement region, said housing having the characteristic such that the application of force at said skin-engagement region causes deformation about said skin-engagement region, said deformation defining a limited range of region motion,
- movable lance means aligned with said access aperture for piercing skin, said lance means having a puncture point having an armed position within said housing, a neutral position within said housing and a propelled position wherein said puncture point is at the exterior of said housing,
- spring means coupled to said lance means for displacing said puncture point in and out of said housing, from said armed position to said propelled position, said spring means having a helical spring encircling said puncture point when said puncture point is in said neutral position, and
- catch means for releasably holding said spring means in a condition in which potential energy is stored for said displacing of said puncture point, said spring means coupled to said housing in a manner to release said spring means in response to said deformation, said spring means moving toward a relaxed condition after said displacing to locate said puncture point in said neutral position spaced apart from said skin-engagement region by a distance exceeding said limited range of region motion.

* * * * *